US007597406B2

(12) United States Patent
Judy, II

(10) Patent No.: US 7,597,406 B2
(45) Date of Patent: Oct. 6, 2009

(54) MULTI-LOCATION TRACTOR TRAILER PNEUMATIC CONNECTIONS

(75) Inventor: Gerald Neil Judy, II, Putaski, VA (US)

(73) Assignee: Volvo Trucks North America, Greensboro, NC (US)

( * ) Notice: Subject to any disclaimer, the term of this patent is extended or adjusted under 35 U.S.C. 154(b) by 480 days.

(21) Appl. No.: 11/526,527

(22) Filed: Sep. 25, 2006

(65) Prior Publication Data

US 2007/0235275 A1 Oct. 11, 2007

Related U.S. Application Data

(60) Provisional application No. 60/791,611, filed on Apr. 11, 2006.

(51) Int. Cl.
*B60T 13/00* (2006.01)
(52) U.S. Cl. .......................................................... 303/7
(58) Field of Classification Search ................. 303/3.7, 303/15, 33–68, 84.1–84.2
See application file for complete search history.

(56) References Cited

U.S. PATENT DOCUMENTS

| 3,241,888 A | * | 3/1966 | Ternent | 303/7 |
| 3,304,131 A | * | 2/1967 | Bueler | 303/29 |
| 3,929,381 A | * | 12/1975 | Durling | 303/118.1 |
| 3,992,064 A | * | 11/1976 | Carton et al. | 303/7 |
| 4,258,959 A | * | 3/1981 | Knight et al. | 303/7 |
| 5,042,883 A | * | 8/1991 | McCann et al. | 303/7 |
| 5,046,786 A | * | 9/1991 | Johnston et al. | 303/7 |
| 7,396,089 B2 | * | 7/2008 | Bennett et al. | 303/119.2 |
| 2004/0183364 A1 | * | 9/2004 | Marsh et al. | 303/7 |
| 2007/0296267 A1 | * | 12/2007 | Walker et al. | 303/15 |

* cited by examiner

*Primary Examiner*—Christopher P Schwartz
(74) *Attorney, Agent, or Firm*—Martin Farrell

(57) ABSTRACT

A tractor truck configured for towing trailers of different air connection configuration. The truck has a first and a second tractor protection valve, each configured to be located on the tractor at a location remote from the other. Each tractor protection valve location is proximate a typical position at which a mating connection on a trailer will be located when hitched to the tractor. The truck also has a selector which is operator-transitionable between a first configuration in which the first tractor protection valve is activated to supply pressured air to an interconnected trailer and a second configuration in which the second tractor protection valve is activated to supply pressured air to a different interconnected trailer.

20 Claims, 3 Drawing Sheets

MULTI-LOCATION TRACTOR TRAILER PNEUMATIC CONNECTIONS

This application claims the benefit of U.S. Provisional Patent Application No. 60/791,611, filed Apr. 11, 2006.

FIELD

The present invention relates to tractor trailers, and in particular, to systems that enable efficient pneumatic interconnection between a tractor and variously configured trailers.

BACKGROUND

Heavy tractor-type trucks are designed to tow trailers, and semi-trailers, having large loads for transport of goods, supplies or other freight. Generally, trailers have no engine of their own and are pulled behind a tractor truck. Heavy trucks are generally configured around a chassis frame which forms the superstructure of the vehicle which typically includes an engine, drive train, drive wheels and steering wheels, among other primary components. Further, an occupant cab is supported generally above a front portion of the chassis frame. These tractors also usually have a horse shoe shaped device, also known as a fifth wheel, located toward the rear of the chassis frame and which is designed to receive a protrusion, or kingpin, from the trailer for "hitching" different trailers, one at a time, to the towing tractor.

In current designs, tractor trucks and trailers rely on air pressure rather than hydraulic fluid for brake control. This increases the ease of coupling and uncoupling the trailer from the truck, while also reducing some of the problems associated with hydraulic systems.

In order to supply the trailer with air for control of the brakes and/or other systems, air hoses from the truck must be connected with the trailer. Generally trucks have two types of air lines that must be interconnected with the trailer for controlling trailer brakes and which are often referred to as service and emergency air lines. Air pressure in the service air lines, also known as control or signal lines, is controlled by the foot brake or a trailer hand brake. In general, the air pressure in the control or signal lines varies depending on how much the foot brake is depressed by the operator/driver. The emergency air lines, also known as supply lines, supply air to the trailer's air tank(s) and control the trailer's emergency brakes. Emergency brakes are designed to be applied if the pressure in the emergency lines fall below a particular value.

Pneumatic interconnection between the tractor and the trailer is facilitated using well known "glad-hand" devices. For connection, a glad hand from the truck can be coupled or mated with a glad hand from the trailer thereby providing an air-tight seal and a secure physical connection. Also, there can be a glad hand for the different types of air hoses, including one or more for the service lines as well as the emergency line.

Trailers can be designed to connect with the air lines of the tractor at any of a number of locations, but the two typical possibilities are at the backside of the truck cab or near the rear end of the chassis frame. In order to facilitate attachment in either of these typical locations, today's tractor trucks employ sets of glad-hand connections at each of the two positions. Due to these different sets of glad hand connections, one or the other will be connected to a particular trailer, but never both. Furthermore, the set that is connected to the trailer must be provided pressured supply air, while it is preferable that none is supplied to the other non-connected set of glad hands.

In the past, in order to switch between the available connections in dependence upon to which the trailer was connected, manual reconfiguration of the air delivery system by the operator was required. For example, multiple valves might have to be turned or plugged, hose connections disconnected and reconnected elsewhere, as well as other actions that may need to be taken depending on the number and design of the involved interconnections. Such requirements increase the amount of labor and time costs for an operator. They also increase the possibility that the connections will not always be properly achieved with obvious negative results.

Therefore, what the present solution appreciates and addresses is the need for a simple, but effective system for shifting between the several possible connections with minimal manual involvement on the operator's part.

SUMMARY

The presently disclosed solution, in at least one embodiment, takes the form of a heavy truck having a pressured air-supply system and configured for activating one of a plurality of trailer air-supply connections on the truck. Each of the trailer air-supply connections are configured for interconnection with a pressured air receiver on a trailer hitched to the truck. The heavy truck exemplarily takes the form of a tractor configured for towing trailers of different configurations, with the tractor having a chassis frame upon which an occupant cab is carried and a rear frame portion to which variously configured trailers can be hitched.

The heavy truck includes a first and a second tractor protection valve, each configured to be located on the tractor at a location remote from the other and so that each protection valve location is proximate a typical position at which a mating connection on a trailer will be located when the particular trailer is hitched to the tractor. In a preferred embodiment, the first tractor protection valve is located at the backside of the occupant cab and the second protection valve is located proximate the rear frame portion of the chassis frame. While only first and second tractor protection valves are specifically called out, it should be appreciated that any number of valves above two might be included.

As disclosed, each tractor protection valve has at least one signal air inlet and at least one supply air inlet on the upstream side of the particular protection valve. Like signal air inlets on each of the first and second protection valves are interconnected in open fluid communication with each other and with a common signal air source. The tractor protection valves, on a downstream side thereof, each have a tractor-to-trailer signal line hose and a supply line hose fluidly connected thereto. Further, each of these hoses terminates in a glad hand configured for mating and sealing engagement with a matched trailer-connected glad hand. Typically, these glad hand connections are configured to break apart, without damage, when tension in the line exceeds a certain threshold. This prevents the hoses from being torn apart should an operator fail to disconnect the mated hose ends when the trailer is unhitched from the tractor.

The truck also includes a selector positioned on the tractor, with the selector being operator-transitionable between a first configuration in which the first tractor protection valve is activated to supply pressured air to an interconnected trailer and a second configuration in which the second tractor protection valve is activated to supply pressured air to a differently configured and interconnected trailer.

It should be appreciated that the above description constitutes examples of implementations of the currently disclosed solutions to the problems associated with needing to accommodate pneumatic interconnection at multiple locations on a towing tractor truck when differently designed trailers (at least with respect to location of pneumatic interconnection) are encountered.

BRIEF DESCRIPTION OF THE DRAWINGS

The accompanying drawings variously illustrate aspects of the presently disclosed inventions. It should be appreciated that the illustrated embodiments are exemplary only, and do not serve as limitations to the protection. The drawings do, however, constitute part of the disclosure of the specification, and thereby contribute to, and provide support for the patented invention(s). In the figures.

DETAILED DESCRIPTION

The present invention will now be described and disclosed in greater detail. It is to be understood, however, that the disclosed embodiments are merely exemplary of the invention and that the invention may be embodied in various and alternative forms. Therefore, specific structural and functional details disclosed herein are not to be interpreted as limiting the scope of the claims, but are merely provided as an example to teach those persons skilled in these arts to make and use the invention(s) delimited by the patented claims, and equivalents thereto.

Figure 1:
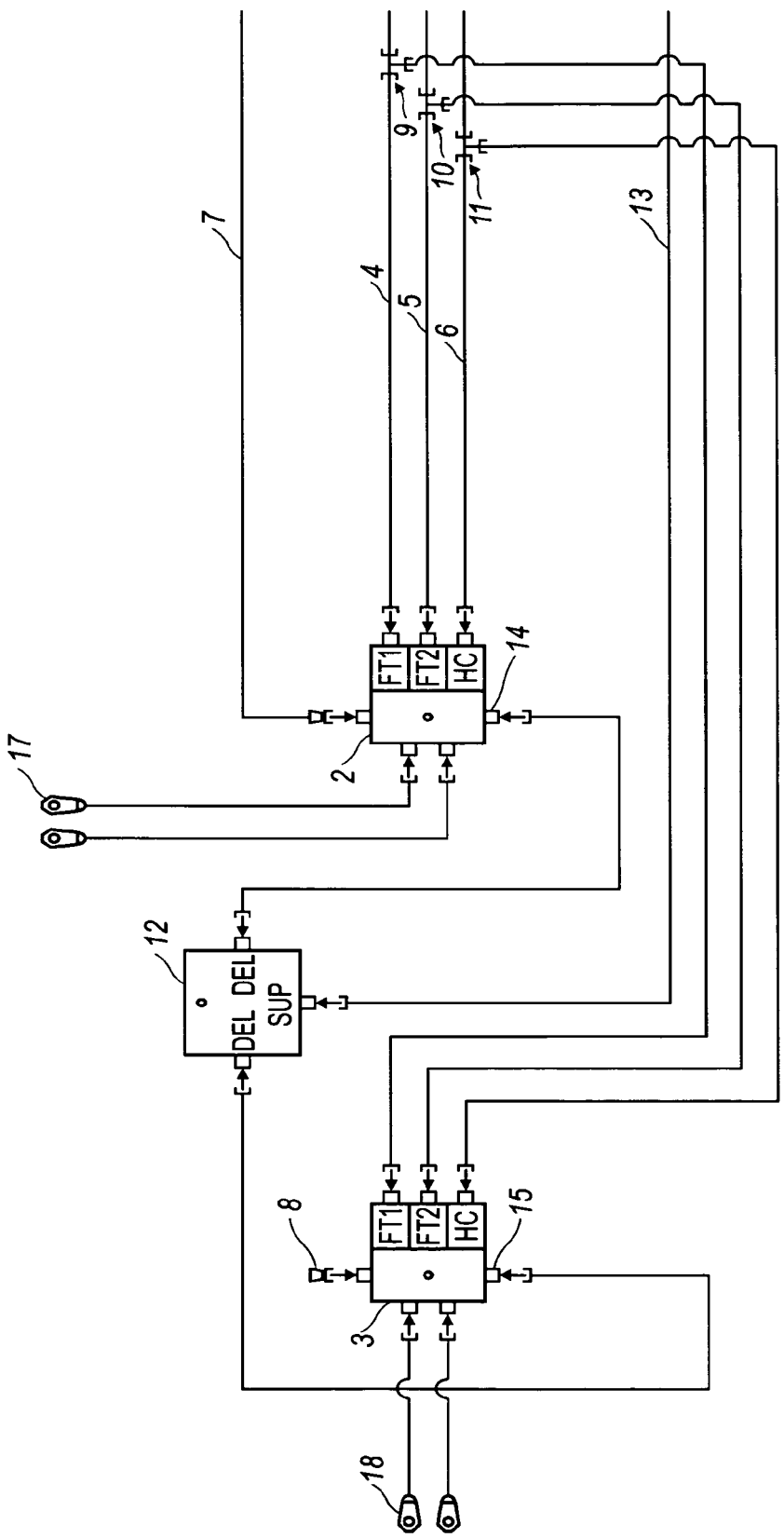
FIG. 1 is a schematic of the dual connection system.

One embodiment of the presently disclosed pressured air-supply system 1 is illustrated in schematic form in FIG. 1. As shown, there are two tractor protection valves, a tractor cab protection valve 2 and a tractor frame protection valve 3, each located on the tractor remote from the other.

As explained above, the trailers that might be hitched to a tractor can have their air receiving connectors at any of a number of typical locations, but with the two most common locations being either proximate the back of the occupant cab of the tractor or lower, near the chassis frame, usually toward the rear end of the frame. In order to facilitate connection at either of these two locations, in a preferred embodiment, the cab protection valve 2 is located at or proximate to the backside of the occupant cab and the frame protection valve 3 is located at or proximate to the rear frame portion of the chassis frame. Each protection valve has input lines and output lines for providing air to the trailer for braking. Protection valves are generally used to control air pressure by opening and closing to allow and prevent air flow, respectively. A function of the protection valve is to protect the tractor's braking system from downstream leaks or ruptures, and can also be used to close off the tractor's air system when disconnecting a trailer from a truck.

The tractor frame protection valves 2, 3 have an open, or activated position, as well as a closed, or inactivated position in order to control air pressure. In many protection valves, a piston is provided which slides within the valve to different positions to block or to allow pressured air from the truck's signal line(s) to the trailer for the control of the trailer brakes. When air pressure is supplied to move the piston, as through a supply line 21, the piston slides to an open position thereby allowing pressured air from a signal line 19 to pass through the protection valve 2, 3 and further to glad hands 17, 18 attached to the end of downstream air lines. Therefore, when a driver depresses the brake pedal on the tractor, the trailer brakes are also applied. When there is no supply pressure applied to move the piston and activate the protection valve, pressured air from the truck's signal lines is prevented from passing through the protection valve.

It should be appreciated that the protection valves 2, 3 are of a generally fail-safe design. That is, the piston is biased to the closed configuration of the protection valve if sufficient supply air is not available. When the valve 2, 3 is closed, the emergency brakes of an associated trailer will typically be automatically applied.

Therefore, if the air pressure in the supply line 21 falls too low, the protection valve 2, 3 will close, while at the same time, the trailer's emergency brakes will be applied. The above described configuration and valve performance is best illustrated in FIGS. 3A and 3B were the cab 2 and frame 3 protection valves are generically represented by an exemplary tractor protection valve 20.

Figure 3A:
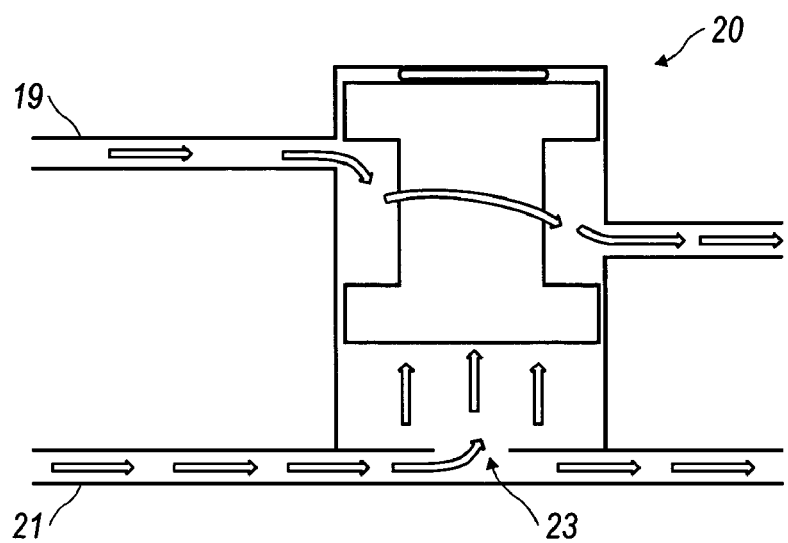
FIG. 3A is a cutaway representation of a protection valve in an activated configuration.

The exemplary tractor protection valve 20 is shown in an open position in FIG. 3A. As depicted, control or signal line 19 directs air to the tractor protection valve 20, and furthermore, supply line 21 supplies air to the tractor protection valve through port 23. The air pressure from the supply line 21 forces piston 22 up into an open position, allowing air from signal line 19 to pass through the tractor protection valve 20. Supply air is conveyed through the protection valve 20, typically to a reservoir tank on a connected trailer where pressured air is stored and used for regular pneumatic brake operation, but can also be used to apply emergency brakes of the trailer should the supply of air be discontinued or otherwise compromised.

Figure 3B:
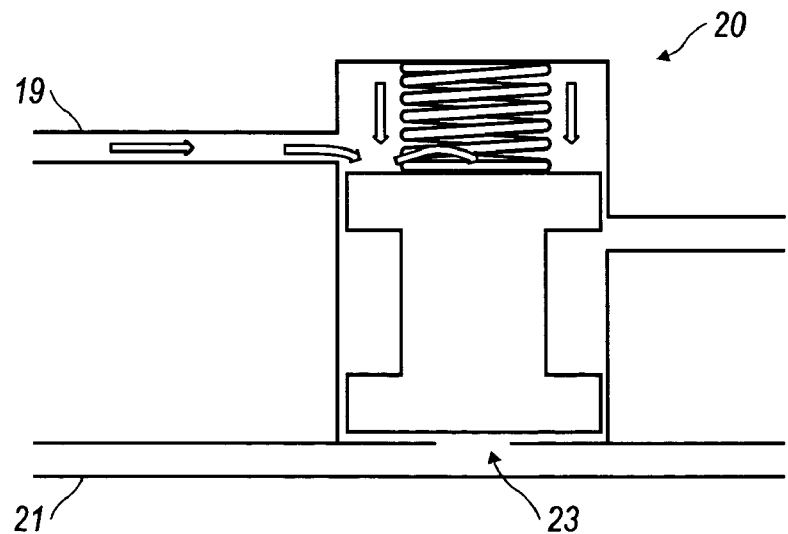
FIG. 3B is a cutaway representation of a protection valve in a closed configuration.

Alternatively, FIG. 3B illustrates the tractor protection valve 20 in a closed position. As shown, no air is passing through the supply line 21 to the tractor protection valve 20, and therefore the piston 22 remains in a closed position. This prevents pressured air in signal line 19 from passing through the tractor protection valve 20.

In a preferred embodiment of the system, and as shown in FIG. 1, the first and second tractor cab protection valves 2, 3 have upstream input control or signal air lines which are connected to supply air and which in FIG. 1 take the form of a cab primary control line 4, a cab secondary control line 5, and a cab hand control line 6. In other embodiments there may be fewer or a greater number of air lines. There may be only one control line or several. In some embodiments, whenever the brake is applied, primary and secondary lines are pressurized, or alternatively only the primary is actuated. Furthermore, when pressurized, even if no air passes through the cab protection valve 2, the stoplight line 7 can still be affected to activate the stoplights, or brake lights. Therefore, because the stop light can be actuated regardless of which protection valve is activated, this allows the frame stop light valve 8 to be plugged, and actuation of the stop light accomplished by use of line 7. In other embodiments, different lines may be pressurized upon braking, and the stoplight can be provided alternative ways, such as for example by use of frame protection valve 3 alone or with cab tractor protection valve 2.

As input air is supplied by primary, secondary, and hand signal lines 4, 5, and 6 respectively, the air is passed through to both the tractor cab protection valve 2 and the tractor frame protection valve 3. This is accomplished by using a series of T-valves or through-connections which intake air from one direction and pass the air in two downstream directions, one to the cab protection valve 2 and the other direction to the tractor frame protection valve 3. The primary signal line 4 passes pressurized air through the primary T-valve 9 and the secondary signal line 5 passes pressurized air through the secondary T-valve 10, and the hand signal line can pass pressurized air through the tertiary T-valve 11. Thus, by use of such T-valves, the signal air inlets of each protection valve can be interconnected in open fluid communication with each other and can have a common signal air source. There may be other methods for enabling open fluid communication between the protection valves such as where the hose carrying the signal air can merely diverge without use of a T-valve. Thereafter, the air can be prevented from passing through the cab protection valve 2 or the frame protection valve 3 unless such valves are activated.

Each protection valve (cab protection valve 2 and frame protection valve 3) has one or a plurality of tractor-to-trailer supply or control lines which connect to, or terminate in one or a plurality of glad hands. There may be one or a plurality of tractor-to-trailer supply lines and therefore may terminate in one or a plurality of glad hands. Each protection valve 2, 3 can have one or a plurality of tractor-to-trailer signal line hose terminating in one or a plurality of glad hands.

Figure 2:
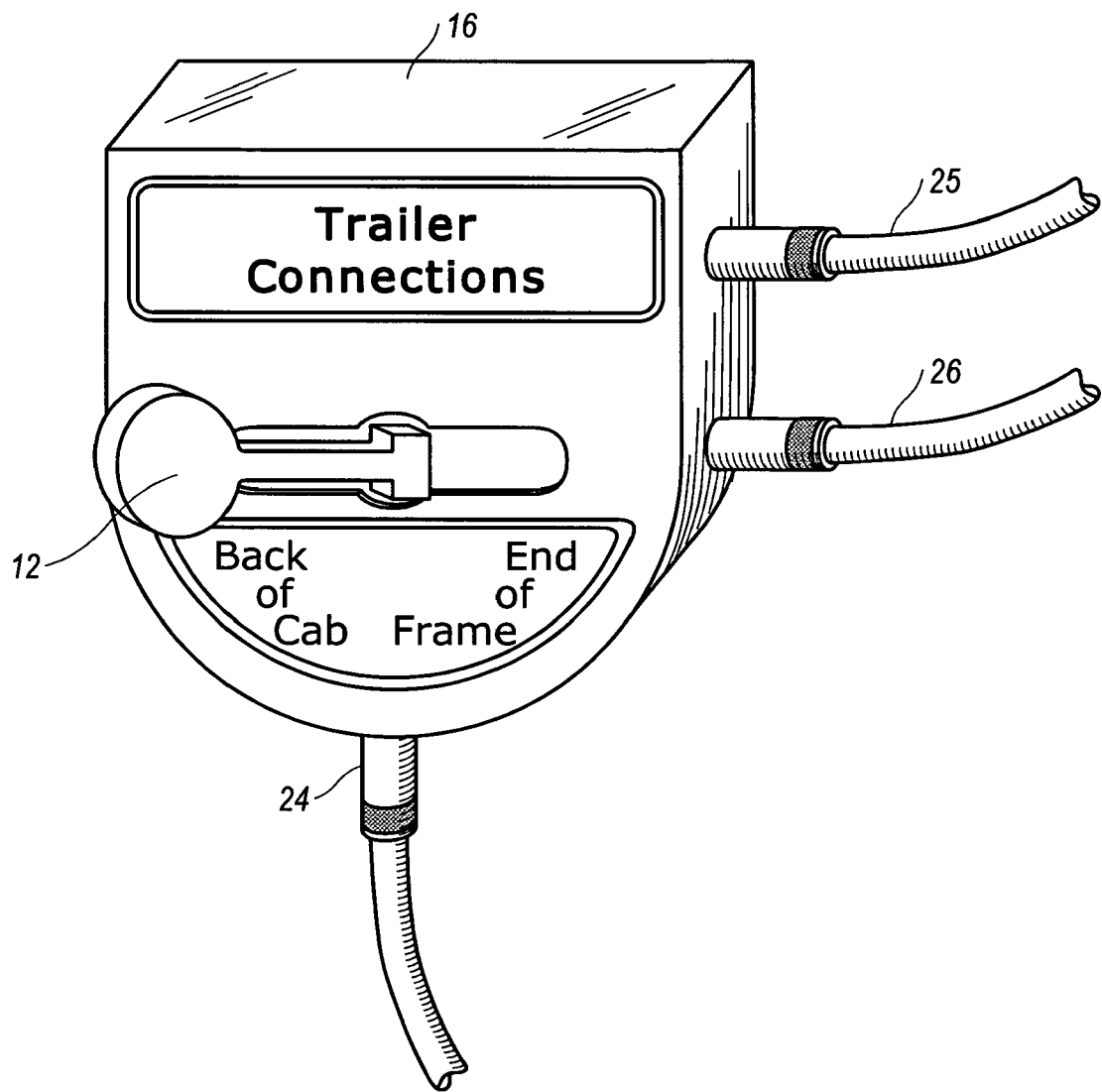
FIG. 2 is an illustrative representation of a diverter valve of the system.

Activation of the cab protection valve 2 or the frame protection valve 3 is controlled by a selector 12, wherein one embodiment is illustrated in FIG. 2. The selector can be any arrangement that accommodates the transition between each protection valve by the action of the operator. In a preferred embodiment, the selector 12 further comprises a three-way pneumatic diverter valve 16 which can be used to affect the transition between each protection valve. The diverter valve 16 can have an inlet for receiving pressured supply air and two outlets, each outlet supplying pressured supply air to a different tractor protection valve.

The diverter valve 16 receives air pressure from the tractor supply line 13, and can divert the air to either the cab tractor supply port valve 14 attached to the cab protection valve 2, or to the frame tractor supply port valve 15 attached to the frame protection valve 3, thereby activating the respective protection valves. In this way, by manipulating the selector 12, the operator can transition between a first configuration in which a first tractor protection valve 2 is activated to supply pressured air to an interconnected trailer and a second configuration in which a second tractor protection valve 3 is activated to supply pressured air to a different interconnected trailer. The tractor supply line is usually provided with air when the trailer is connected to the tractor truck.

When air pressure from the supply line 13 is applied to a tractor supply port valve, it in turn allows air to pass through the protection valve 2, 3 to which it is attached, and is therefore activated. The function of the system is such that no air is allowed through either protection valve 2, 3 until air pressure is applied to its respective tractor emergency port 14, 15. Thus, when a protection valve 2, 3 is activated, pressured air from the signal lines 4, 5, 6 will pass to the trailer. Furthermore, pressured air from the supply line 13 will also pass through to the trailer.

Therefore, according to some embodiments of the current invention, by manipulating the selector 12, an operator can activate cab protection valve 2 or frame protection valve 3. The selector 12 can be made variably configurable using a hand-manipulatable lever as shown in FIG. 2. The selector 12 can also be a button, trigger, switch, rod, projection, and can be electronic or manual, or any other mechanism which accommodates the transition between each protection valve. The selector 12 can also be conveniently placed proximate the cab (inside or out), and with a preferred location being on the left hand (driver's side) outside corner of the cab. Alternatively, the selector 12 can be positioned proximate the driver's seat inside the cab and thereby allowing the operator to conveniently manipulate the selector.

Also illustrated in FIG. 2 is the diverter valve 16 which has an inlet 24 and two outlets 25 and 26. Outlets 25 and 26 provide pressured air from the supply line to the protection valves. Diverter valve 16 can affect the transition between each protection valve by diverting air to either tractor emergency port valve 14 or 15. The diverter valve 16 can be located anywhere on the truck including proximate to the cab, or on the left hand outside corner of the cab, or proximate to the driver's seat inside the cab. It should be appreciated that the diverter valve 16 need not necessarily be proximate the selector 12 which is manipulated by the operator.

The following exemplarily illustrates one of the embodiments of the invention. If a trailer is attached to the back of the cab portion, an operator could actuate the selector 12 such that air pressure would be directed through the diverter valve 16 to the cab tractor supply port 14. This in turn would activate and open the cab tractor protection valve 2 thereby enabling the provision of pressured air to the cab glad hands 17 from lines 4, 5, and/or 6 for controlling the brakes. Furthermore, pressured air from the supply line 13 which passed through the diverter 16 would also be supplied to the glad hands 17, for example, to control the emergency brakes of the trailer. At the same time that the cab protection valve 2 is activated, no air pressure from the supply line would be diverted by the diverter valve 16 to the frame tractor supply port valve 15. As a result, the frame tractor protection valve 3 would not be activated.

Conversely, the operator can actuate the selector such that supply air pressure is directed through the diverter valve 16 to the cab tractor supply port 15. This in turn would activate the frame tractor protection valve 3. Pressured air can then pass through the protection valve 3 from lines 4, 5, and/or 6 to the frame glad hands 18, thereby allowing control of the trailer brakes. Furthermore, pressured air from the supply line 13 which passed through the diverter 16 would also pass to the glad hands 18, for example, to control the emergency brakes of the trailer. At the same time, pressure would not be provided to the tractor port valve 14, and therefore the cab tractor protection valve 2 would be deactivated, preventing air from passing through to the cab glad hands 17. In this way, an operator can easily transition between modes depending on whether the hitched trailer is designed to connect with a truck's air supply from the back of the cab or from the end of the truck frame.

Both cab glad hands 17 and frame glad hands 18 are configured for a mating sealing engagement with a matched trailer-connected glad hand. In this way, pressured air can be delivered to the trailer regardless of how it may be configured.

What is claimed is:

1. A heavy truck including a pressured air-supply system configured for activating one of a plurality of trailer air-supply connections on the truck, said heavy truck comprising:
   a tractor configured for towing trailers of different configurations, said tractor having a chassis frame having a front frame portion upon which an occupant cab is carried and a rear frame portion to which variously configured trailers are hitchable;
   a first tractor protection valve and a second tractor protection valve, each configured for interconnection with a pressured air receiver on a connected trailer to supply pressured air thereto, each located on the tractor at a location remote from the other and wherein each tractor protection valve location is proximate a typical position at which a mating connection on a trailer will be located when hitched to the tractor; and a selector positioned on the tractor, said selector being operator-transitionable between a first configuration in which said first tractor protection valve is activated to supply pressured air and a second configuration in which said second tractor protection valve is activated to supply pressured air.

2. The heavy truck as recited in claim 1, wherein said first tractor protection valve is located at a backside of the occupant cab.

3. The heavy truck as recited in claim 1, wherein said second tractor protection valve is located proximate the rear frame portion of the chassis frame.

4. The heavy truck as recited in claim 1, wherein said first tractor protection valve is located at a backside of the occupant cab and said second tractor protection valve is located proximate the rear frame portion of the chassis frame.

5. The heavy truck as recited in claim 4, wherein each of said first and second tractor protection valves comprises a signal air inlet and a supply air inlet.

6. The heavy truck as recited in claim 5, wherein said selector further comprises a diverter valve having an inlet for receiving pressured supply air and two outlets, one each fluidly connected to the supply air inlets of said first and second tractor protection valves for distributing pressured air thereto in dependence upon the configuration of said diverter valve.

7. The heavy truck as recited in claim 5, wherein the signal air inlet of each of said first and second tractor protection valves are interconnected in open fluid communication with each other and with a common signal air source.

8. The heavy truck as recited in claim 1, further comprising:
a brake light actuator fluidly connected with at least one of said tractor protection valves and configured to be actuated by applied signal air pressure at said at least one tractor protection valve.

9. The heavy truck as recited in claim 1, further comprising:
a brake light actuator connected in fluid communication with each of said tractor protection valves and configured to be actuated by applied signal air pressure at either of said tractor protection valves.

10. The heavy truck as recited in claim 1, further comprising:
each of said tractor protection valves having a tractor-to-trailer signal line hose fluidly connected thereto, said tractor-to-trailer signal line hose terminating in a glad hand configured for mating sealing engagement with a matched trailer-connected glad hand.

11. The heavy truck as recited in claim 1, further comprising:
each of said tractor protection valves having a tractor-to-trailer supply line hose fluidly connected thereto, said tractor-to-trailer supply line hose terminating in a glad hand configured for mating sealing engagement with a matched trailer-connected glad hand.

12. The heavy truck as recited in claim 1, wherein said selector is positioned proximate a driver's seat inside said cab whereby easy operator manipulation is facilitated.

13. A system configured for activating one of a plurality of trailer air-supply connections on a heavy truck, said system comprising:
a first tractor protection valve and a second tractor protection valve, each configured to be located on a heavy truck at locations remote from one another and each configured for interconnection with a pressured air receiver on a connected trailer; and
a selector operator-transitionable between a first configuration in which said first tractor protection valve is activated to supply pressured air and a second configuration in which said second tractor protection valve is activated to supply pressured air.

14. The system as recited in claim 13, wherein each of said first and second tractor protection valves comprises a signal air inlet and a supply air inlet.

15. The system as recited in claim 14, wherein said selector further comprises a diverter valve having an inlet for receiving pressured supply air and two outlets, one each fluidly connected to the supply air inlets of said first and second tractor protection valves for distributing pressured air thereto in dependence upon the configuration of said diverter valve.

16. The system as recited in claim 14, wherein the signal air inlet of each of said first and second tractor protection valves are interconnected in open fluid communication with each other and with a common signal air source.

17. The system as recited in claim 13, further comprising:
a brake light actuator fluidly connected with at least one of said tractor protection valves and configured to be actuated by applied signal air pressure at said at least one tractor protection valve.

18. The system as recited in claim 13, further comprising:
a brake light actuator connected in fluid communication with each of said tractor protection valves and configured to be actuated by applied signal air pressure at either of said tractor protection valves.

19. The system as recited in claim 13, further comprising:
each of said tractor protection valves having a tractor-to-trailer signal line hose fluidly connected thereto, said tractor-to-trailer signal line hose terminating in a glad hand configured for mating sealing engagement with a matched trailer-connected glad hand.

20. The system as recited in claim 13, further comprising:
each of said tractor protection valves having a tractor-to-trailer supply line hose fluidly connected thereto, said tractor-to-trailer supply line hose terminating in a glad hand configured for mating sealing engagement with a matched trailer-connected glad hand.

* * * * *